United States Patent [19]

Weissman

[11] 4,251,210
[45] Feb. 17, 1981

[54] DENTAL POSITIONING DEVICE

[75] Inventor: Bernard Weissman, New York, N.Y.

[73] Assignee: IPCO Corporation, White Plains, N.Y.

[21] Appl. No.: 128,840

[22] Filed: Mar. 10, 1980

Related U.S. Application Data

[63] Continuation-in-part of Ser. No. 070,247, Aug. 27, 1979.

[51] Int. Cl.³ ............................................... A61C 3/02
[52] U.S. Cl. ........................................ 433/76; 433/215
[58] Field of Search ....................... 433/215, 75, 72, 76

[56] References Cited

U.S. PATENT DOCUMENTS

| | | | |
|---|---|---|---|
| 1,321,130 | 11/1919 | Schlueter et al. | 433/76 |
| 3,508,334 | 6/1970 | Weissman | 433/76 |
| 3,822,472 | 7/1974 | Garfinkel | 433/215 |
| 4,177,565 | 12/1979 | Heasley | 433/75 |

*Primary Examiner*—Robert Peshock
*Attorney, Agent, or Firm*—Friedman, Goodman & Teitelbaum

[57] ABSTRACT

A dental positioning device for facilitating the accurate placement of a drill guide on teeth in order to drill spaced apart aligned bores in which a dental retaining splint is to be received. The positioning device is formed of a continuous wire including a U-shaped top section lying in a horizontal plane with an anchoring pin vertically extending from one arm of the top section, and a loop depending from the other arm thereof, the loop also lying in a horizontal plane. The anchoring pin is inserted through the axial opening of a first tubular member upwardly extending from a drill guide and further inserted into a first hole drilled in the tooth. The loop fits around a second tubular member also extending upwardly from the drill guide and spaced from the first tubular member. The axial opening in the second tubular member is then used to drill a second hole accurately spaced apart from the first hole. After the positioning device and drill guide are removed, a dental retaining splint is then inserted into the drilled holes. The structure of the positioning device permits easy removal thereof from the teeth, where the positioning device can be used to remove the drill guide therewith. The bight portion of the U-shaped top section provides a visual indication as to the proper position of the drill guide.

9 Claims, 6 Drawing Figures

DENTAL POSITIONING DEVICE

RELATIONSHIP TO OTHER APPLICATIONS

This application is a continuation-in-part application of U.S. Ser. No. 070,247 filed on Aug. 27, 1979 for a "Dental Retaining Splint".

BACKGROUND OF THE INVENTION

The present invention relates to dentistry in general, and more particularly to a dental positioning device for facilitating drilling of bores in teeth in order for the bores to receive a dental retaining splint for the reinforcement and retention of dentition in the mouth.

The use of dental splints for reinforcing natural teeth is well known in the art. However, prior art dental splints have been accompanied by serious limitations. For example, frequently the securing pins for the splint structure are disposed in horizontal parallelism. As a consequence, the use of such splints have been restricted mainly to anterior teeth. Also, the complexity involved in installing such splints have also restricted their use.

In the aforementioned co-pending parent application, there has been described a new dental retaining splint which is formed of a bar-like member having tubular members extending perpendicularly therefrom with the tubular members having axial openings extending therethrough. The splint is first temporarily held, by means of a temporary wax, in a channel formed in adjacent teeth. The tubular members then function as guides for a drill to form pilot holes in the teeth. The splint is then removed and the pilot holes function as lead holes for the formation of enlarged bores to receive the tubular members therein for retaining the adjacent teeth in a fixed position. The splint is then repositioned in the channel so that the tubular members are disposed in the bores formed therefor. An inlay fills in the channel and covers the splint in the final procedure step.

In utilizing such improved dental retaining splints, the accuracy and alignment of the bores is an important factor. This is one of the reasons why the dental retaining splint, which serves as the drill guide, is inserted in the channel and retained by means of the wax. The wax holds the splint sufficiently firm to utilize it as an accurate drill guide.

However, the use of the temporary wax requires additional time, effort, and further manipulation in the patient's mouth. Also, occasionally, if the wax does not hold securely enough, it is possible for the splint to slide within the channel and thus the holes which are formed may not be accurately spaced to subsequently receive the splint for its final retention of the teeth.

Furthermore, it might occasionally be necessary to drill two holes in subsequent operations. Accordingly, after the first hole is drilled, it might be necessary to remove the drill guide so as to be able to take x-rays or to provide for further manipulation or checking of the accuracy of the location of the hole. Subsequently, the drill guide must be repositioned into the mouth at the same location in order to drill the second hole. However, once the drill guide has been removed, it is difficult to reposition it accurately in order to align the second hole so that it will be able to accurately receive the retaining splint.

Although the dental retaining splint when used as a drill guide may only have two tubular members, it is possible to form a continuous chain of splints which will fit into a channel which extends across more than two adjacent teeth. Accordingly, by using one of the retaining splints as a drill guide in a leap frog manner, it is possible to form a continuous series of holes. Subsequently, the splints will be inserted into these continuous holes, the splints having straight line segments in order to proximate the curvature of the teeth in that portion of the mouth.

With such splints extending over a series of teeth, it is necessary to space the new hole accurately from the previous hole. By using a splint as the drill guide with only two tubular sections, it is necessary to continuously remove it and reposition it at the next adjacent location. Accordingly, accurate relocation is necessary for proper positioning of the splint. Such would be difficult when the splint has to be continuously held by means of the temporary wax.

SUMMARY OF THE INVENTION

Accordingly, it is an object of the present invention to provide a dental positioning device for facilitating use of a drill guide in order to drill spaced apart, aligned bores in teeth.

Another object of the present invention is to provide a dental positioning device for use with a drill guide in order to facilitate use of the drill guide without the necessity of using temporary wax for retaining the drill guide in position on the teeth.

A further object of the present invention is to provide a dental positioning device which will facilitate utilization of a drill guide over an extended length of the dentition.

Still another object of the present invention is to provide a dental positioning device for use with a dental retaining splint of the type described in the aforementioned parent application.

Yet another object of the present invention is to provide a dental positioning device for use with a drill guide, whereby a hole to be drilled is accurately positioned with respect to a previous hole already drilled in the teeth.

An added object of the present invention is to provide a dental positioning device which facilitates utilization of a drill guide and which accurately positions holes drilled in the teeth, wherein the positioning device provides a visual indication as to the proper position of the drill guide.

These objects are achieved in accordance with a preferred embodiment of the present invention wherein the dental positioning device comprises a top member for overlying a portion of the occlusal surface of the teeth. An anchoring pin extends from the top member. The anchoring pin is received in a first bore drilled into the teeth. A retaining member also extends from the top member at a spaced distance from the anchoring pin. The retaining member engages a tubular member of a drill guide so that a second bore can be drilled into the teeth using the tubular member as the guide.

In an embodiment of the present invention, the positioning device is formed of a continuous wire with the top member being of a U-shaped configuration and lying in a horizontal plane. The anchoring pin vertically extends from the end of one arm of the U-shaped top member. The retaining portion includes a vertical section extending from the other arm. The vertical section terminates in a loop lying in a horizontal plane, the vertical section being shorter in length than the anchoring pin.

In utilizing the positioning device, the anchoring pin is inserted through an axial opening in one tubular member of the drill guide and is further inserted into a first hole drilled into the teeth. The loop of the retaining member fits around the next adjacent tubular member and holds it in place for use as a guide for drilling the next adjacent hole. The bight portion of the U-shaped top member provides a visual indication as to the proper position of the drill guide. Furthermore, the positioning device is easily removed from the teeth, and can remove the drill guide therewith.

BRIEF DESCRIPTION OF THE DRAWINGS

With the above and additional objects, and advantages in view, as will hereinafter appear, this invention comprises the devices, combinations and arrangements of parts hereinafter described by way of example and illustrated by the accompanying drawings of a preferred embodiment in which.

In the various figures of the drawings, like reference characters designate like parts.

DETAILED DESCRIPTION OF THE PREFERRED EMBODIMENT

Figure 1:
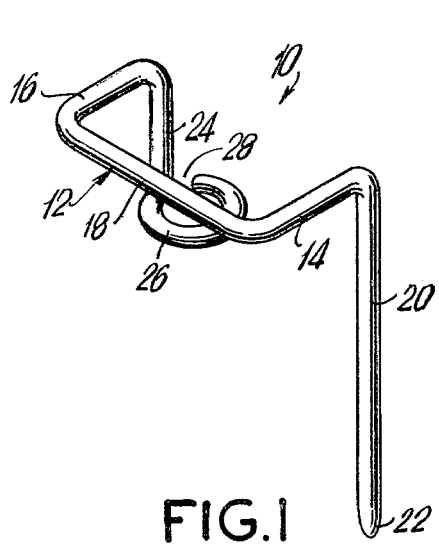
FIG. 1 is a perspective view of the dental positioning device in accordance with the present invention.
Figure 2:
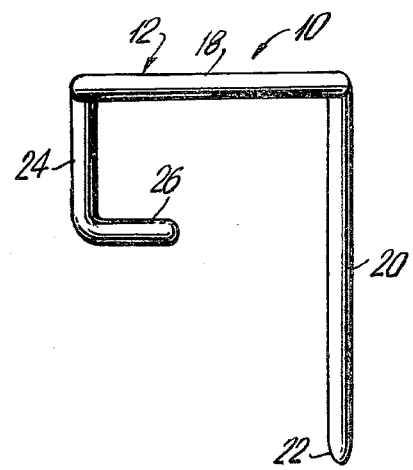
FIG. 2 is a front view of the positioning device.
Figure 3:
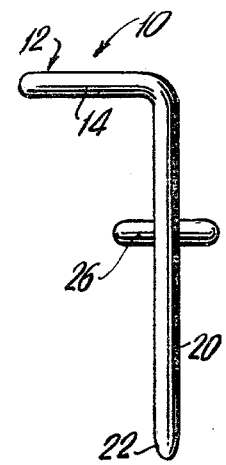
FIG. 3 is a side elevational view of the positioning device.

Referring now to the drawings, FIGS. 1-3 show a dental positioning device 10 according to the present invention. The positioning device 10 is a one piece, continuous wire or rod having a U-shaped member 12 lying in a substantially horizontal plane and including the arms 14 and 16 interconnected by the bight portion 18.

Downwardly extending from the arm 14 is a vertical section defining an anchoring pin 20 and terminating at its distal end in a point 22. Downwardly extending from the other arm 16 is a vertical section or rod 24 terminating in a loop 26 which also lies in a horizontal plane. The loop 26 is shown as being open ended to provide the space 28. However, if desired, the space 28 can be closed to provide a complete loop.

As clearly indicated in the FIGS. 2 and 3, the arms 14, 16 are of equal length and are parallel to each other. Furthermore, the downwardly extending anchoring pin 20 and vertical rod 24 are perpendicular to their associated arms 14, 16 and are also parallel to each other, lying in a substantially vertical plane. The loop 26 is spaced predetermined distances from both the arm 16 and the anchoring pin 20.

Figure 4:
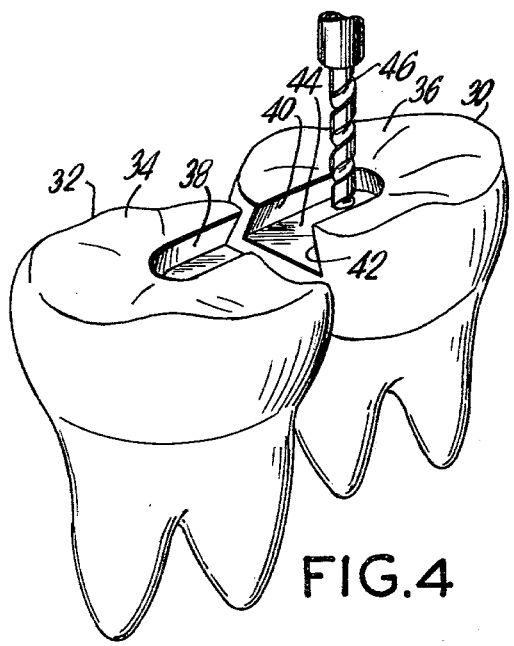
FIG. 4 is a perspective view illustrating two adjacent teeth provided with a channel to receive a dental retaining splint, and showing the first step in utilizing the present positioning device, specifically the drilling of a first hole in the channel.
Figure 5:
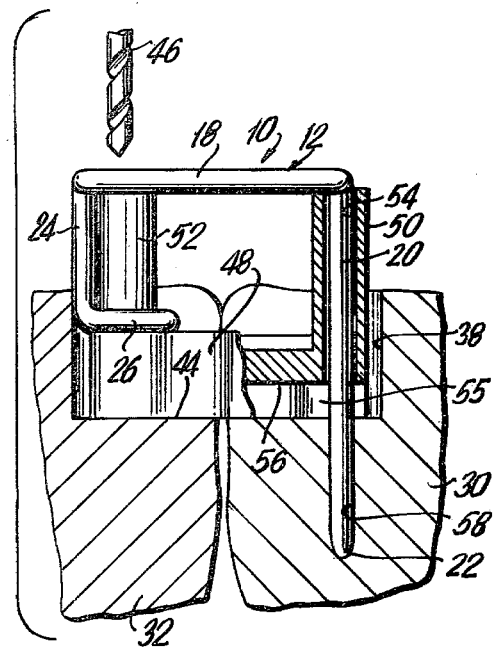
FIG. 5 is an elevational view, partly in section, illustrating the use of the dental positioning device in aligning a drill guide for drilling of a subsequent hole.
Figure 6:
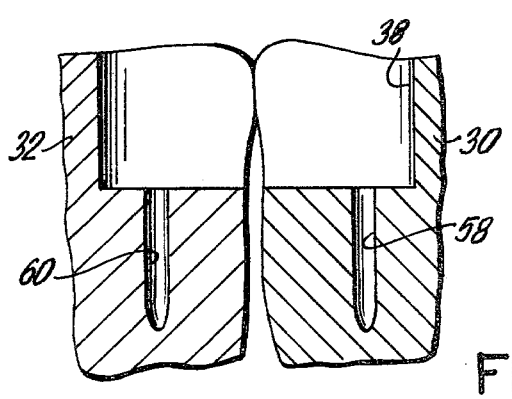
FIG. 6 is an elevational sectional view illustrating the two holes extending from the channel provided in the teeth after the positioning device and the dental retaining splint, or drill guide, have been removed.

Referring now to FIGS. 4-6, the operation of the present positioning device 10 will be described. FIG. 4 shows a pair of adjacent teeth 30, 32, such as for example the adjacent bicuspids. However, it is understood that the present invention is equally applicable to and between other adjacent teeth, such as the cuspids, the molars, etc. In each occlusal surface 34, 36 of the crowns, a connecting channel 38 is formed therebetween in a conventional manner. Preferably, the walls 40, 42 of the channel 38 are tapered to provide a wide base 44 at the bottom of the channel where the tapered walls act to retain the inlay of dental material within the channel, as described in the parent application. It is understood that the channel 38 is oversized to be larger than the dental splint which is to be inserted.

After the channel 38 is formed, a drill bit 46 is utilized to drill the initial hole in the teeth, and specifically through the base 44 of the channel. The position of the initial hole can be judged by means of the eye and specifically spaced adjacent one edge of the channel. The exact location of the first hole is not of critical importance since it is the accuracy of the spacing between the holes which is of more importance in order to properly receive the retaining splint.

Although FIG. 4 shows that the first hole is drilled without the aid of a drill guide, it should be understood that even the first hole could be drilled with the aid of a drill guide. Such drill guide could either be any of a conventional number drill guides or, alternately, could be the dental retaining splint of the aforementioned parent application which will subsequently be described.

After the initial hole has been drilled in the teeth, the dental retaining splint of the aforementioned parent application can be temporarily placed in the channel. It should be noted that the splint is placed directly on the base 44 of the channel without the use of any wax for holding the splint in place.

The splint itself includes a bar-like body member 48 having outwardly extending tubular members 50, 52 extending perpendicularly therefrom. The tubular members are spaced apart a predetermined distance corresponding to the distance between the anchoring pin 20 and the center of the loop 26. Furthermore, the length of the arms 14, 16 is greater than the radius of the tubular members 50, 52, preferably being much greater so that the bight portion 18 acts as a handle for placing and removing the positioning device. The tubular member each include an axial opening 54 therethrough. The bar-like member can be formed of various configurations, such as an inverted V-shape or an H-shape, to provide the space 55 beneath the base 56 of the bar-like member so as to be able to receive some of the dentinal material carried to the surface by the drill bit 46.

With the retaining splint positioned in the channel 38 with the tubular members 50, 52 extending upwardly, as shown in FIG. 5, the positioning device 10 is inserted. The anchoring pin 20 is placed in the axial opening 54 in the tubular member 50 and passed therethrough so that it enters into the hole 58 which was initially drilled. The loop 26 is positioned around the other tubular member 52, and pushed downwardly to rest against the bar-like member 48. Additionally at the same time, a portion of the arm 14 is pushed downwardly to rest against the top of the tubular member 50. It is noted, that the length of the vertical section 24 is predetermined so that the loop 26 rests against the bar-like member 48 when the portion of the arm 14 engages against the top of the tubular member 50.

It is noted, that because of the specific arrangement of the structure of the positioning device 10, the bight portion 18 provides a visual indication as to the position of the drill guide. As clearly shown in FIG. 5, the bight portion 18 is parallel to the bar-like member 48 when mounted on the drill guide. Thus, the bight portion 18 can be viewed when the bar-like member 48 is disposed in the channel 38. Accordingly, when drilling the second hole, the bar-like member 48 should be in a horizontal position, which can be ascertained by viewing the bight portion 18. If the bight portion 18 is not in a horizontal position, the second hole should not be drilled at this time, where a correction should be made, such as reforming the channel 38 or merely cleaning out the channel 38 so that the bar-like member 48 can be placed in the proper horizontal position.

With the anchoring pin 20 holding the one tubular member 50 in place directly above the first hole 58 that was drilled, the positioning device 10 will accurately maintain the second tubular member 52 at a proper position in the channel 38 so that a second hole 60 can be drilled therein by inserting the drill bit 46 through the tubular member 52 and drilling through the base 44 of the channel with the tubular member 52 acting as a guide for the drill bit 46. In this manner, the spacing and alignment of the two holes 58, 60 in the channel 38, as shown in FIG. 6, will be suitable so that the tubular member of the splint, when inverted, can be received in the holes, when enlarged, and retained properly in place.

It should be understood that the holes 58, 60 that are drilled can either be used for splints having small tubular members, or can be used as pilot holes. The pilot holes are further enlarged by means of reaming or drilling the holes so as to provide the larger bores that are needed to retain the properly sized retaining splint, which are shown in FIG. 5.

It should also be appreciated, that although the dental retaining splint of the aforementioned parent application has been used for drilling the holes, other types of drill guides could likewise be utilized. In fact, a drill guide having a single tubular member could also be utilized. The anchoring pin could be placed in the first hole drilled and the loop can be placed around the single tubular drill guide to properly position it for drilling of a second, adjacent hole.

Although a drill guide having only two adjacent tubular members has been shown and described, it should be understood that the drill guide could have more than the two tubular members, as described in the parent application, and accordingly, a plurality of holes could be continuously drilled. In each case, the anchoring pin 20 would be placed in the last hole and the loop 26 would fit around the next adjacent tubular member. As a result each next subsequent hole which is drilled is properly spaced and aligned with respect to the previous hole that is drilled.

It should also be appreciated that although the channel was shown as being drilled into adjacent teeth, should a retaining splint be desired which extends across a plurality of teeth, a larger channel would be drilled. In such cases, it would not be necessary to initially form a drill guide which corresponds to the full length of the retaining splint to be inserted. A short drill guide having only the two tubular sections could be utilized. The drill guide would be moved in leap frog fashion from one hole to the next adjacent hole, in each case the positioning device 10 would be utilized to properly space the next adjacent hole from the last one drilled.

It should also be appreciated that by means of the positioning device, as described, it is not necessary to attach the drill guide or dental retaining splint temporarily by means of the wax. Such temporary retention by means of the wax requires additional time and effort as well as additional manipulation within the patient's mouth. These can all be avoided since the dental guide or retaining splint is held anchored by means of the present positioning device.

The length of the rod or vertical section 24 holding the loop 26 is substantially shorter than the anchoring pin 20 so that the anchoring pin can enter into the first tubular member and the first drilled hole while the loop is held onto the second tubular member as described above. The diameter of the anchoring pin 20 is approximately equal to the inner diameter of the axial opening contained in the tubular member. The inner diameter of the loop 26 is approximately equal to the outer diameter of the tubular member. In this way a tight fit can be obtained by means of the positioning device and accuracy will be achieved.

As stated above, the bight portion 18 acts as a handle for placing and removing the positioning device. Accordingly, with a tight fit arrangement between the positioning device 10 and the drill guide, the bight portion 18 can also be used to place and remove the drill guide therewith. This is particularly useful when it is required to move the drill guide in a leap frog fashion from one hole to the next adjacent hole, as set forth above. Thus, the bight portion 18 functions both as a handle and as a visual indicator.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental positioning device for facilitating an accurate placement of a drill guide on teeth in order to drill spaced apart, aligned bores in which a dental retaining splint is to be received, said positioning device comprising:
   a top member for overlying a portion of the drill guide;
   an anchoring pin extending from said top member for being received in a first bore drilled in the teeth; and
   retaining means also extending from said top member for holding a tubular member of the drill guide so that a second bore can be drilled in the teeth using the tubular member as the guide, said retaining means being suitably spaced from said anchoring pin said retaining means including a vertical rod connected to said top member and terminating in a loop which lies in a horizontal plane, said loop being of a size to encircle and hold the tubular member.

2. A dental positioning device as in claim 1, wherein said top member includes a U-shaped rod having a pair of arms and a bight portion lying in a horizontal plane, said vertical rod of said retaining means extending from one of said arms and said anchoring pin extending from the other arm.

3. A dental positioning device as in claim 2, wherein said positioning device is a one piece continuous rod.

4. A dental positioning device as in claim 1, wherein said vertical rod of said retaining means is shorter in vertical height than said anchoring pin.

5. A dental positioning device as in claim 1, in combination with a drill guide, said drill guide comprising an elongated bar-like member being disposable in a channel extending from a first tooth to at least one adjacent tooth, said bar-like member having at least one tubular member extending perpendicularly therefrom for receiving said retaining means of said positioning device, said tubular member including an axial hole therethrough to function as a guide for a drill during formation of the bores in the teeth.

6. A dental positioning device in combination with a drill guide as in claim 5, wherein said bar-like member has at least two spaced apart tubular members extending perpendicularly therefrom, each of said tubular members including the axial hole therethrough, an outside diameter of said anchoring pin proximating a diameter of the axial hole, and a spacing between said tubular members being substantially the spacing between said anchoring pin and said retaining means, whereby said anchoring pin is received in the axial hole of one tubular member and extends into the first bore while the retaining means holds the other tubular member so that the second bore can be drilled.

7. A dental positioning device comprising:
 a pair of spaced apart arms connected by a bight portion to provide a U-shaped member disposed in one plane, said arms being of equal length and parallel to each other;
 an anchoring pin perpendicularly extending in one direction from one of said arms;
 a rod member perpendicularly extending in said one direction from the other arm, said rod member being parallel to said anchoring pin, said rod member being shorter than said anchoring pin;
 said rod member and said anchoring pin being disposed in a second plane perpendicular to said one plane;
 said rod member terminating in a loop spaced from said other arm and spaced from said anchoring pin, said loop being disposed in a third plane parallel to said one plane; and
 said positioning device being a one piece construction whereby said anchoring pin is receivable in a bore drilled in a tooth and said loop being positionable about a tubular member of a drill guide so that a second aligned bore can be dilled in a tooth using the tubular member as a guide.

8. A method for accurately drilling aligned, spaced apart bores in teeth, comprising:
 drilling a first hole in a tooth;
 positioning a drill guide having tubular guiding portions on the occlusal surface of the teeth with the tubular guiding portions extending upwardly therefrom;
 inserting an anchoring pin portion of a positioning device through an axial opening of a first of said tubular guiding portions of the drill guide and into said first hole, and at the same time mounting a looped portion of said positioning device around a second of said tubular guiding portions of the drill guide; and
 drilling a second hole in a tooth by using an axial opening through the second tubular guiding portion as a drill guide.

9. A method as in claim 8, further comprising the steps of:
 forming a channel across at least two adjacent teeth, and
 temporarily disposing the drill guide having the tubular guiding portions extending therefrom into said channel without the use of any retaining wax.

* * * * *